US00PP18383P2

(12) United States Plant Patent
Utecht

(10) Patent No.: US PP18,383 P2
(45) Date of Patent: Jan. 1, 2008

(54) ***PELARGONIUM* PLANT NAMED 'FISNOW'**

(50) Latin Name: *Pelargonium peltatum*
Varietal Denomination: Fisnow

(75) Inventor: Angelika Utecht, Montabaur (DE)

(73) Assignee: Florfis AG, Binningen (CH)

( * ) Notice: Subject to any disclaimer, the term of this patent is extended or adjusted under 35 U.S.C. 154(b) by 0 days.

(21) Appl. No.: 11/529,118

(22) Filed: Sep. 28, 2006

(51) Int. Cl.
*A01H 5/00* (2006.01)

(52) U.S. Cl. ..... Plt./332
(58) Field of Classification Search ..... Plt./332
See application file for complete search history.

(56) References Cited

PUBLICATIONS

PBR PEL 02045—filed Germany Jun. 27, 2005, published Aug. 15, 2006; granted Nov. 10, 2006.*

* cited by examiner

*Primary Examiner*—Wendy C. Haas
*Assistant Examiner*—Georgia Helmer
(74) *Attorney, Agent, or Firm*—Jondle & Associates, P.C.

(57) ABSTRACT

A new cultivar of *pelargonium* particularly characterized by having small to medium-sized, white to pink, single-type flowers that are self-cleaning with good rain tolerance, floriferous with numerous inflorescences, medium-green foliage, medium-sized to tall, and bushy very well-branched, spreading to trailing plant habit and an early flowering response, is disclosed.

2 Drawing Sheets

Genus and species: *Pelargonium peltatum* L'Héritier.
Variety denomination: 'Fisnow'.

BACKGROUND OF THE NEW PLANT

The present invention comprises a new and distinct cultivar of *pelargonium,* botanically known as *Pelargonium peltatum,* and hereinafter referred to by the cultivar name 'Fisnow'. The new cultivar is a product of a planned breeding program which had the objective of creating new ivy *geraniums* in a variety of colors, having cascading plant habits and numerous small, single-type flowers. 'Fisnow' was discovered as a seedling resulting from the cross of the female parent 'I99-2043-8' (unpatented), a proprietary white to very pale-pink flowered *pelargonium* and the male parent, a white-flowered plant from the commercial and multicolored variety 'Tornado' (unpatented).

The new cultivar was created in 2002 in Hillscheid, Germany and has been asexually reproduced repeatedly by vegetative cuttings in Galdar, Gran Canaria, Spain, and Hillscheid, Germany over a three-year period. It has been found to retain its distinctive characteristics through successive asexual propagations. 'Fisnow' reproduces true to type in successive generations of asexual reproduction.

Plant Breeder's Rights for this cultivar were applied for in Germany on Jun. 27, 2005 and in Canada on Oct. 13, 2005.

SUMMARY OF THE INVENTION

The following are the most outstanding and distinguishing characteristics of this new cultivar when grown under normal horticultural practices in Hillscheid, Germany.

1. Small to medium sized, white to pale-pink, single-type flowers;
2. Floriferous with numerous inflorescences;
3. Medium-green foliage with distinct zonation;

4. A medium to tall-sized, bushy, well-branched, spreading to trailing plant habit;
5. Self-cleaning flowers with good rain tolerance; and
6. An early-season flowering response.

DESCRIPTION OF THE PHOTOGRAPHS

This new *pelargonium* plant is illustrated by the accompanying photographs which show overall plant habit including inflorescences, buds, and foliage of the plant; the colors shown are as true as can be reasonably obtained by conventional photographic procedures. The photographs are of three 30-week-old plants in a hanging-basket in early September and grown under greenhouse and outdoor conditions which approximate those generally used in commercial practice.

DESCRIPTION OF THE NEW CULTIVAR

Figure 1:
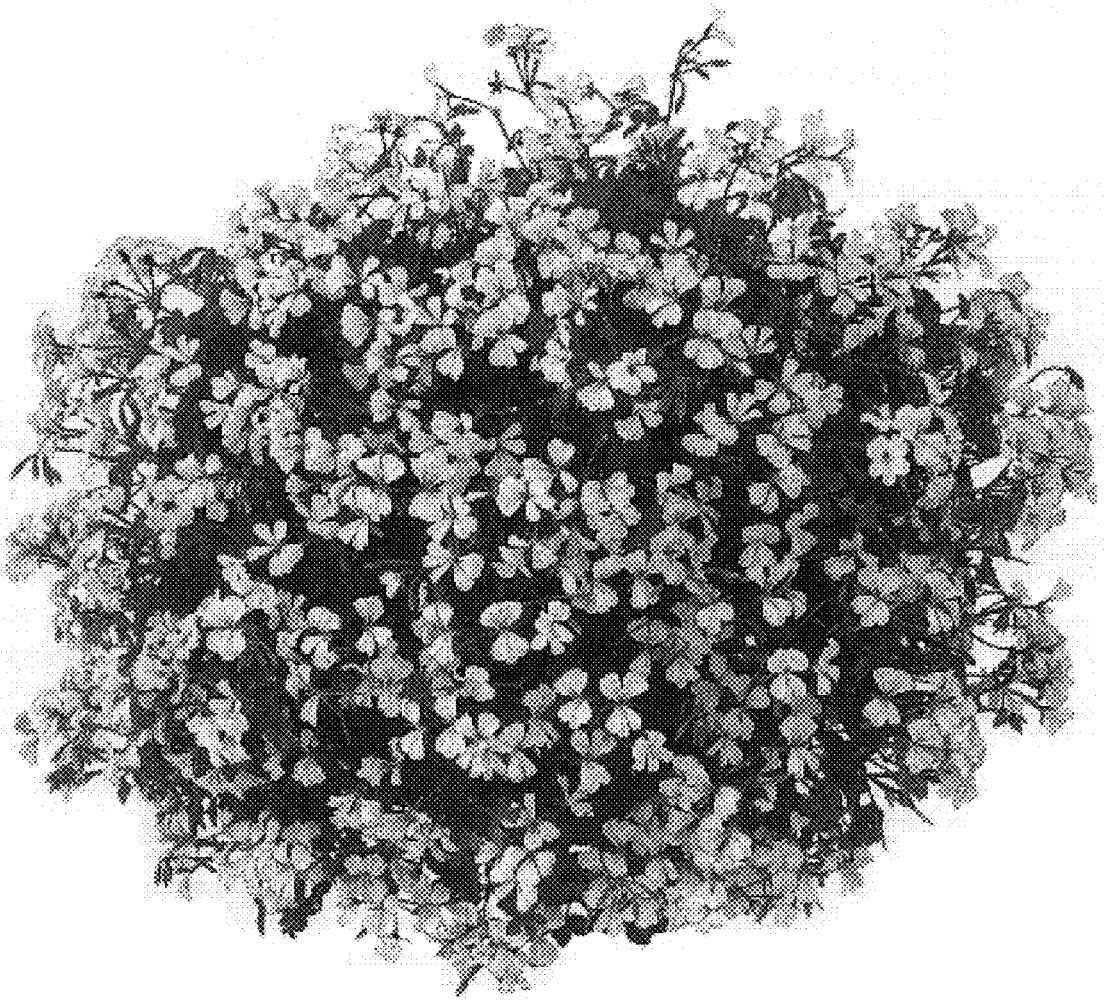
FIG. 1 shows the overall plant habit with blooms, buds and foliage
Figure 2:
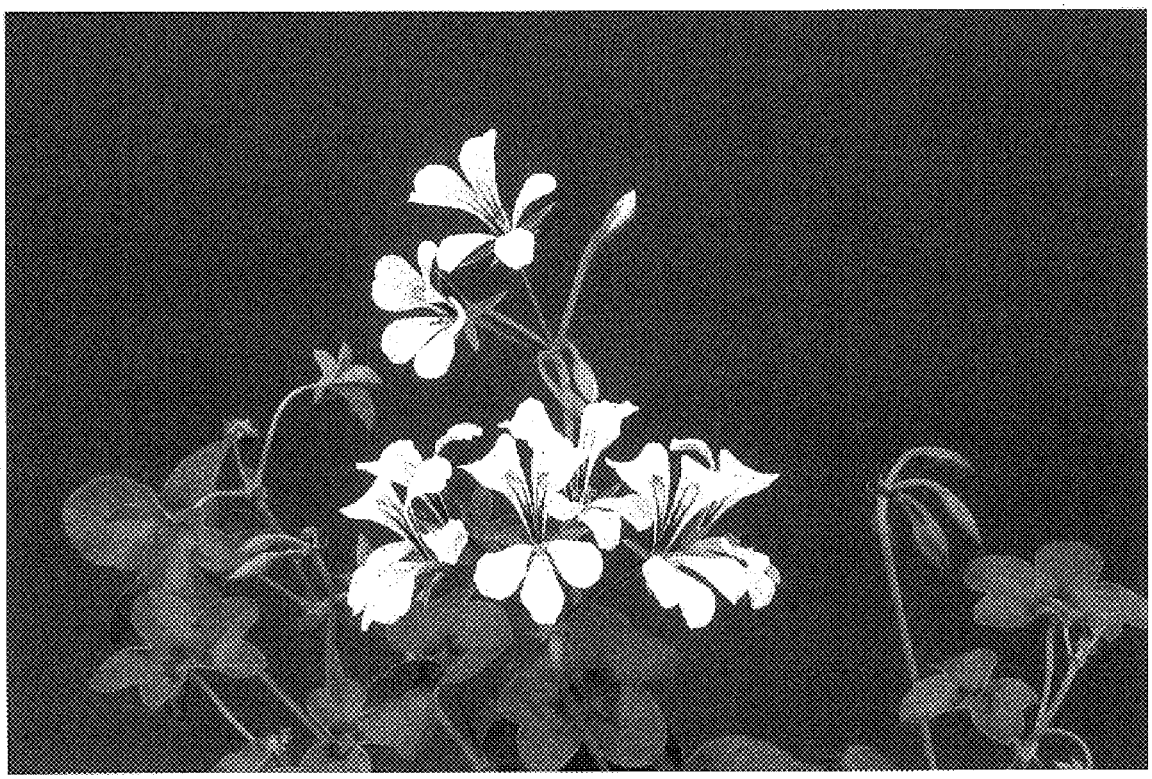
FIG. 2 shows a close-up view of inflorescences

The following detailed description sets forth the distinctive characteristics of 'Fisnow'. The data which define these characteristics were collected from asexual reproductions carried out in Hillscheid, Germany. The plant history was taken on 15-week old plants, pinched once, in 12-cm pots in a greenhouse during late May. Color readings were taken under natural light in mid-May in the greenhouse. Color references are primarily to the R.H.S. Colour Chart of The Royal Horticultural Society of London (R.H.S.) (2001).

DETAILED BOTANICAL DESCRIPTION

Classification:
*Family.*—Geraniaceae.
*Botanical.*—*Pelargonium peltatum* L'Héritier.
*Common name.*—Ivy *geranium.*

Parentage:

*Female parent.*—'I99-2043-8' a proprietary *pelargonium* plant having white to very pale-pink flowers (unpatented).

*Male parent.*—A white-flowered plant from the commercial and multi-colored variety 'Tornado' (unpatented).

Plant:

*Form.*—Shrub, self-branching, initially spreading, later trailing.

*Branching habit.*—15 to 20 branches per plant.

*Height* (*measured from base of the stem to the tips of the branches, excluding the inflorescence*).—10.6 cm.

*Width* (*plant diameter*).—45.5 cm.

*Plant spread at end of summer* (*about* 30 *weeks old*).—70 cm to 80 cm.

*Time to produce a finished flowering plant.*—About 11 to 12 weeks after planting rooted cuttings in Hillscheid, Germany.

*Outdoor plant performance.*—Plants continuously flower; a count in late summer in Hillscheid, Germany produced about 30 to 40 inflorescences per plant.

Leaves:

*Arrangement.*—Initially alternate, opposite at flowering stems.

*Immature leaf color.*—Upper surface: RHS 143A. Lower surface: RHS 143B.

*Mature leaf color.*—Upper surface: RHS 137C (medium-green). Lower surface: RHS 137D.

*Zonation color.*—RHS 166A (brown) narrow, but with medium distinctness.

*Zonation diameter.*—Inner diameter of ring: 1.5 cm. Band or belt of zonation: 0.5 cm.

*Size.*—Length: 5.2 cm. Width: 7.0 cm.

*Shape.*—Ivy-shaped (palmatisect) with relatively deep/strong lobes, usually 5 lobes, occasionally only 3 main lobes, and with a gap between the lowest lobes.

*Apex.*—Rounded to obtuse tips of lobes.

*Base.*—Cordate.

*Margin.*—Entire.

*Texture.*—Upper surface is smooth, leathery and somewhat glossy.

*Petioles.*—Color: RHS 143A (grass-green). Length: 3 cm to 5 cm. Diameter: 0.25 cm to 0.30 cm. Texture: Smooth, nearly glabrous.

Stems:

*Stem color.*—RHS 143B (green).

*Length.*—25 cm to 30 cm.

*Diameter.*—0.3 cm to 0.4 cm.

*Internode length.*—3.0 cm to 4.0 cm.

*Texture.*—Appears smooth, nearly glabrous.

Flower bud: (just before petals unfold).

*Shape.*—Elliptical, narrow.

*Size.*—Length: 2.3 cm to 2.5 cm. Width: 0.8 cm.

*Color of sepals.*—RHS 144A (yellow-green), partly infused with anthocyanin.

*Anthocyanin color.*—RHS 181B.

*Color of petals.*—RHS N155D.

Inflorescence:

*Inflorescence type.*—An umbel composed of 6 to 7 flowers.

*Umbel.*—Shape: Irregular or funnel-shape. Diameter: Up to 9.3 cm. Height (depth): 5.2 cm.

*Lastingness of umbel on the plant.*—About 12 to 14 days.

*Peduncle.*—Color: RHS 137D (medium-green). Length: 10.7 cm. Diameter: 0.20 cm to 0.25 cm. Texture: Appears smooth, very few hairs.

*Pedicel.*—Color: Partly RHS 143B (light-green), partly RHS 181A (purple). Length: 3.3 cm. Diameter: 0.15 cm. Texture: Nearly glabrous, a few hairs.

Corolla:

*Shape of corolla.*—Zygomorphic, with the upper petals and lower petals separated by a wide gap, roughly funnel-shaped with the petals slanting upright.

*Form.*—Single-type.

*Diameter.*—4.7 cm.

*Depth.*—2.0 cm to 2.5 cm.

*Number of petals.*—5.

*Petaloids.*—None.

*Lastingness of individual flowers on plant.*—5 to 7 days at 18° C.

*Fragrance.*—None.

Petals:

*Shape.*—Spatulate to narrow obovate.

*Apex.*—Rounded to truncate, possibly weakly retuse.

*Base.*—Acute or attenuate.

*Margin.*—Entire.

*Texture.*—Smooth, slightly glossy.

*Upper petals.*—Length: 3.0 cm to 3.2 cm. Width: 1.5 cm. Color: Upper surface: RHS 155D (white) to RHS 75D (pale white-pink). Lower surface: RHS 155D (white) to RHS 69C or RHS 69D. Markings: Two strong purple veins, RHS 71B, at the base RHS 71A.

*Lower petals.*—Length: 2.2 cm to 2.3 cm. Width: 1.2 cm to 1.3 cm. Color: Upper surface: RHS N155B to RHS 69D to RHS N155B (white to pale-pink). Lower surface: RHS 69D to RHS N155B. Markings: Absent.

Sepals:

*Number.*—5.

*Color* (*both surfaces*).—RHS 143C (light-green) with a RHS 181A (brown) spot at the largest sepal.

*Length.*—0.9 cm to 1.0 cm.

*Width.*—Largest upper sepal: 0.5 cm. Other sepals: 0.2 cm to 0.3 cm.

*Shape.*—Ensiform to lanceolate.

*Apex.*—Acute.

*Base.*—Fused.

*Margin.*—Entire.

*Texture.*—A few relatively long hairs.

Reproductive organs:

*Androecium.*—Number of anthers: 5 to 7. Filament length: 0.5 cm to 0.9 cm. Filament color: Mainly RHS 155D (white) to RHS 68B (pink) at upper end. Pollen color: RHS 25A (orange). Pollen amount: Little, not always developed.

*Gynoecium.*—Pistil: Number: 1. Length: 1.2 cm. Stigma color: RHS 68B to RHS 67C (purple-pink). Stigma shape: Usually 5-lobed. Style color: RHS 155A (white) near base, to RHS N66C (pink) at upper end. Style length: 0.5 cm. Style shape: Filiform (filament-like) with the lobes of the stigma slanting upright and at right angles.

Fruit and seed set: Weak, mainly from late summer to fall: whole fruit with 'beak' about 3.0 cm to 3.5 cm in length, often with 4 seeds; seed grain oblong, 0.4 cm to 0.5 cm in length; 0.2 cm in diameter, with spiral 'tail' (pappus).

Disease and insect resistance: No particularly resistance or susceptibility has been observed; good rain tolerance.

COMPARISON WITH PARENTAL AND COMMERCIAL CULTIVARS

'Fisnow' differs from the female parent 'I99-2043-8' (unpatented) by having a more compact plant habit with shorter internodes and an earlier flowering response than 'I99-2043-8'.

'Fisnow' differs from the male parent 'Tornado' (unpatented) by having mainly purple pedicles while 'Tornado' has mainly green pedicels. In addition, 'Fisnow' has somewhat larger leaves with stronger zonation, less branches and thicker stems than 'Tornado'. Also, 'Fisnow' flowers with a slightly stronger pale-pink hue than 'Tornado'.

'Fisnow' differs from the commercial variety 'PAC White Compact Cascade' (unpatented) by having whiter flowers with a weaker hue of pink color and foliage with somewhat stronger zonation than 'PAC White Compact Cascade'.

I claim:

1. A new and distinct cultivar of *pelargonium* plant as shown and described herein.

* * * * *